United States Patent [19]

Budge et al.

[11] Patent Number: 4,810,807

[45] Date of Patent: Mar. 7, 1989

[54] HYDROGENATION OF MALEIC ANHYDRIDE TO TETRAHYDROFURAN

[75] Inventors: John R. Budge, Cleveland Hts.; S. Erik Pedersen, Solon, both of Ohio

[73] Assignee: The Standard Oil Company, Cleveland, Ohio

[21] Appl. No.: 214,788

[22] Filed: Jul. 5, 1988

Related U.S. Application Data

[63] Continuation-in-part of Ser. No. 107,198, Oct. 13, 1987.

[51] Int. Cl.$^4$ .................................................. C07D 307/08
[52] U.S. Cl. .................................................... 549/508
[58] Field of Search ........................................ 549/508

[56] References Cited

U.S. PATENT DOCUMENTS

| | | | |
|---|---|---|---|
| 3,580,930 | 5/1971 | Miya et al. | 549/325 |
| 3,829,448 | 8/1974 | Kanetaka et al. | 549/325 |
| 3,853,922 | 12/1974 | Yamaguchi et al. | 549/508 |
| 3,890,361 | 6/1975 | Kanetaka et al. | 549/325 |
| 3,894,054 | 7/1975 | Miya | 549/508 |
| 3,948,805 | 4/1976 | Michalczyk et al. | 549/325 X |
| 3,994,928 | 11/1976 | Michalczyk et al. | 549/325 |
| 4,001,282 | 1/1977 | Miller | 549/325 |
| 4,006,165 | 2/1977 | Michalczyk et al. | 549/325 |
| 4,011,244 | 3/1977 | Smith | 549/508 |
| 4,025,534 | 5/1977 | Sandhack et al. | 549/325 |
| 4,048,196 | 9/1977 | Broecket et al. | 549/508 |
| 4,052,335 | 10/1977 | Michalczyk et al. | 252/446 |
| 4,083,809 | 4/1978 | DeThomas et al. | 549/325 X |
| 4,268,695 | 5/1981 | Lange et al. | 568/864 |
| 4,301,077 | 11/1981 | Pesa et al. | 549/508 |
| 4,361,710 | 11/1982 | Weitz et al. | 568/864 |
| 4,584,419 | 4/1986 | Sharif et al. | 568/864 |
| 4,613,707 | 9/1986 | Kouba et al. | 568/864 |
| 4,656,297 | 4/1987 | Koula et al. | 549/508 |

FOREIGN PATENT DOCUMENTS

| | | |
|---|---|---|
| 8603189 | 6/1986 | PCT Int'l Appl. |
| 1168220 | 10/1969 | United Kingdom |
| 1293151 | 10/1972 | United Kingdom |
| 2116552 | 9/1983 | United Kingdom |

OTHER PUBLICATIONS

Hoffstadt et al, Preparation of Catalysts III, Elsevier Science Publishers, Amsterdam (1983) pp. 709–721.

*Primary Examiner*—Richard L. Raymond
*Attorney, Agent, or Firm*—D. P. Yusko; D. J. Untener; L. W. Evans

[57] ABSTRACT

A continuous process for the preparation of tetrahydrofuran comprises, in a single-stage process, catalytically hydrogenating the solution which results when at least one of maleic anhydride or succinic anhydride is dissolved in a monohydric aliphatic alcohol in the presence of hydrogen and a catalyst comprising the mixed oxides of copper, zinc and aluminum.

10 Claims, No Drawings

HYDROGENATION OF MALEIC ANHYDRIDE TO TETRAHYDROFURAN

REFERENCE TO RELATED APPLICATIONS

This is a continuation-in-part of application Ser. No. 107,198 filed Oct. 13, 1987, now abandoned.

BACKGROUND OF THE INVENTION

1. Field of the Invention

This invention relates to the preparation of tetrahydrofuran from at least one of maleic anhydride or succinic anhydride. More specifically, this invention relates to a single stage process for the hydrogenation of maleic anhydride or succinic anhydride in alcohol in the presence of a catalyst comprising the mixed oxides of copper, zinc and aluminum to produce high yields of tetrahydrofuran.

2. Description of the Prior Art

Tetrahydrofuran is a useful solvent for natural and synthetic resins and is a valuable intermediate in manufacture of a number of chemicals and plastics.

It is known in the art that tetrahydrofuran may be produced by a number of different methods, the more prominent among them is the dehydration of 1,4-butanediol and the catalytic hydrogenation of furan. Most tetrahydrofuran is, in fact, manufactured in a multi-step sequence starting with the reaction of acetylene and formaldehyde in the presence of a cuprous acetylide complex to form butynediol. The butynediol is hydrogenated to butanediol, which is dehydrated to tetrahydrofuran as indicated above.

In addition, tetrahydrofuran can be prepared by catalytic hydrogenation of maleic acid, fumaric acid and succinic acid, their respective anhydrides and ester derivatives, and butyrolactone.

The instant invention focuses on the production of tetrahydrofuran from maleic anhydride in the presence of an alcohol. A multi-step process for producing tetrahydrofuran from maleic anhydride is described in U.S. Pat. No. 4,584,419. In this patent the ethyl diester of maleic anhydride is produced and then hydrogenated in the presence of a copper-chromite catalyst to yield minor quantities of tetrahydrofuran and larger quantities of 1,4-butanediol and gamma-butyrolactone.

A more direct synthesis of tetrahydrofuran is proposed in British Patent Specification No. 1,293,151, which utilized a two component catalyst system to produce tetrahydrofuran from a solution of maleic anhydride or succinic anhydride in alcohol. The catalyst system is comprised of a hydrogenation catalyst containing copper and at least one other metal element and dehydration catalyst such as acid clay, molybdenum trioxide or silica alumina.

Lastly, tetrahydrofuran and gammabutyrolactone are derived from maleic anhydride or succinic anhydride using nickel base catalysts in U.S. Pat. No. 3,853,922 and U.S. Pat. No. 3,829,448.

The process described in British Patent Specification No. 1,293,151 provides yields of tetrahydrofuran in excess of 90%. However, the remainder of the above-mentioned processes or catalysts, typically results in low yields of tetrahydrofuran and the formation of relatively large amounts of by-products.

Therefore, an object of this invention is to provide a process for producing tetrahydrofuran in high yields while avoiding the formation of undesirable by-products. Another object is to provide an efficient catalyst with which tetrahydrofuran can be produced in high yields in a single hydrogenation step with less by-products. Still another object is to provide a process which can be carried out without the need for the high pressures and high temperatures required in the prior art processes. Still another object is to provide a novel hydrogenation catalyst system which maintains high activity over time.

SUMMARY OF THE INVENTION

The solution which results when at least one of maleic anhydride or succinic anhydride is dissolved in a monohydric alcohol is catalytically hydrogenated to produce tetrahydrofuran in a continuous single stage process. It has been discovered that high yields of tetrahydrofuran are achieved when the hydrogenation catalyst comprises the mixed oxides of copper, zinc and aluminum.

DETAILED DESCRIPTION OF THE INVENTION

The solution which results when at least one of maleic anhydride or succinic anhydride, dissolved in a monohydric alcohol, is hydrogenated to tetrahydrofuran in a single stage process over a catalyst comprising the mixed oxides of copper, zinc and aluminum without inactivation of the catalyst.

REACTANTS

Maleic anhydride and succinic anhydride are, in general, readily soluble in a monohydric alipatic alcohol, with partial formation of a mono-ester. Consequently, a feed stream of the mono esters of maleic anhydride or succinic anhydride also provides the high yields of tetrahydrofuran in the instant process and are included within the scope of this invention as equivalents of the anhydrides dissolved in alcohol.

All monohydric alcohols are suitable as long as the anhydride is sufficiently soluble therein and it is otherwise system compatible. Preferred suitable monohydric alcohols are the monohydric aliphatic alcohols and more preferred are the $C_1$-$C_{20}$ branched or straight-chain aliphatic alcohols, such as, for example, methanol, p- and iso-propanol, n- and iso-butanol, hexanols, etc. or mixtures thereof. In particular, $C_4$ alcohols, such as n- or iso-butanol, are most preferred for the process of this invention because these alcohols allow for ester product separation. However, higher alcohols, such as $C_{10}$ alcohol, have a lower volatility and are preferable on some circumstances.

The maleic anhydride or succinic anhydride can be dissolved in the alcohol continuously or discontinuously, in a conventional acid-resistant apparatus. It is known that partial esterification of the maleic anhydride occurs upon dissolution. If necessary, the heat of reaction generated on formation of these mono-esters (in the case of iso-butanol it is about 33 kJ/mol) can be easily removed. Complete formation of the mono-ester is not necessary for any of the solvents.

Advantageously, the solutions are prepared at room temperature or moderately elevated temperature, for example at 15° to 60° C. In general, the molar ratio of anhydride to alcohol is 1:0.1 to 1:50, and preferably 1:1 to 1:30. It is advantageous if the alcohol is used in stoichiometric amounts, i.e. 1 mole of maleic anhydride to 2 moles of alcohol. Better conversion of the anhydride are achieved if the alcohol is used in stoichiometric excess, e.g., up to molar ratios of the anhydride to the alcohol of 1:20, preferably 1:2 to 1:15. The use of a 5 to 95 weight percent, preferably 10–80 weight percent, strength by weight solution of anhydride in an alcohol is particularly appropriate. This corresponds, in the case of maleic anhydride or butanol, to a molar ratio of maleic anhydride:butanol of 1:5.3.

Where the maleic anhydride or succinic anhydride is contained in a vaporous stream, such as the reactor effluent from the catalytic oxidation of n-butane in air, the maleic anhydride or succinic anhydride can be dissolved in the alcohol using a "quench" column. Typically, such a quench system is a vertical column in which the maleic anhydride or succinic anhydride containing vapor is brought into contact with the alcohol flowing countercurrent to the vapor (i.e. vapor flowing upwards contacts an alcohol flowing downward). In using such a "quench" system higher molecular weight alcohols (e.g. $C_{10}$ alcohols) are preferable.

The maleic anhydride or succinic anhydride in alcohol solution, also referred to as the solution mixture in this specification, is fed continuously together with hydrogen, and without further treatment or working-up, over the hydrogenation catalyst.

CATALYST

The instant process for the hydrogenation of at least one of maleic anhydride or succinic anhydride in a monohydric alcohol to produce tetrahydrofuran is characterized by the use of a hydrogenation catalyst comprising the mixed oxides of copper, zinc and aluminum. This catalyst may be used alone or in combination with a cocatalyst comprising the mixed oxides of copper and chromium.

Typically, the hydrogenation catalyst comprising the mixed oxides of copper, zinc and aluminum are of the general formula:

$$Cu_1Zn_bAl_cM_dO_x$$

where

M is at least one element selected from Groups IIA thru IIIA, Group VA, Group VIII, Ag, Au, Groups IIIB thru VIIB, the Lanthanum Series, and Actinium Series of the Period Table of Elements $0.001 < b < 500;$
$0.001 < c < 500;$
$0 \leq d < 200;$ and x is the number of oxygen atoms necessary to satisfy the valency requirements of the other elements.

As used herein, the Periodic Table of Elements refers to the commonly accepted version as appears in *The Condensed Chemical Dictionary*, 10th Edition, G. G. Hawley, Van-Nostrand Reinhold Company (1981), p.789.

Typically, the catalysts of the present invention may be prepared by conventional coprecipitation techniques such as those described in *Preparation of Catalysts III*, Hoffstadt et al., Elsevier Science Publishers B. V., (1983) pgs. 709–721. In general, the coprecipitation technique comprises coprecipitation of an aqueous metal nitrate solution at elevated temperatures with an alkali or ammonium carbonate or bicarbonate. The precipitated material is then filtered off, washed and then dried at elevated temperatures (120° C.) and calcined at a temperature of 350°–400° C. The catalyst could also be impregnated with one or more promoter elements prior to the calcination step. Alternatively, promoter elements could be incorporated in the precipitation step.

The catalyst may be reduced at temperatures between 150°–500° C. by flowing hydrogen, or hydrogen mixed with an inert gas (e.g. $N_2$) over the catalyst. Other reducing gas mixtures also be used including carbon monoxide, carbon monoxide/hydrogen, and carbon monoxide/water.

PROCESS PARAMETERS

At least one of maleic anhydride or succinic anhydride together with the monohydric alcohol are co-fed with a hydrogen-containing gas over the hydrogenation catalyst, at elevated temperature and pressures. The hydrogen to anhydride feed ratio may vary from about 10:1 to about 1000:1, and is preferably between about 100:1 and 500:1.

Typically, the hydrogen containing gas is commercially pure hydrogen. However, the hydrogen containing gas feed may also contain nitrogen, oxygen, any gaseous hydrocarbon (e.g. methane), as well as gaseous oxides of carbon, (e.g. carbon monoxide, carbon dioxide).

The hydrogen containing gas can be introduced into the hydrogenation apparatus together with the solution mixture, co-currently or counter-currently. Hydrogenation can also be carried out by bubbling hydrogen through the solution mixture phase. Preferably, the hydrogen containing gas and the solution mixture are passed in co-current flow over a fixed catalyst bed located in a hydrogenation furnace. An alternative and also preferred method for combining the reactants is to first feed the maleic anhydride alcohol solution to a vaporizer with the hydrogen containing gas also being fed to a vaporizer. The anhydride in alcohol solution vaporizes and mixes with the hydrogen containing gas. This mixture is then fed to the reactor containing the hydrogen-atom catalysts.

In order to be able, where necessary, to remove the heat of hydrogenation more effectively and to achieve a uniform temperature profile over the entire catalyst bed, unreacted hydrogen and also a part of the material discharged from the hydrogenation reaction can be recycled to the hydrogenation furnace.

The quality of the results of the hydrogenation reaction is partially dependent on the throughput of the solution mixture over the catalyst. The throughput for the successful performance of the reaction can vary within wide limits. For example, the liquid hourly space velocity (LHSV) between about 0.1 to 100 per hour.

The hydrogenation can be carried out at pressures of 1 to 500 atmospheres, preferably at 10 to 100 atmospheres, more preferably at about 15–50 atmospheres hydrogen pressure. Suitable reaction temperatures are 150° to 400° C. and are preferably 200°–325° C.

Slight losses in activity of the catalyst during the reaction period can be compensated by slowly raising the temperature. The activity of the catalyst remains constant over a long period of time in spite of exposure to carboxylic acids formed as intermediates and to the water produced in reaction.

Hydrogenation furnaces of conventional construction can be used for carrying out the process of this invention, provided that they are designed for the requisite temperatures and pressures and are made of acid-resistant material.

The reaction products are advantageously separated by fractional distillation. Thereby, the solvent is recovered unchanged and can be reused to dissolve maleic anhydride. Similarly, the n-butanol formed as a by-product can be recycled as the solvent. 1,4-butanediol formed in small amounts, is recovered and can be fed to some appropriate use. Other by-products formed in small amounts, such as, for example, succinic acid dialkyl esters and butyrolactone, are advantageously returned to the hydrogenation stage. Small proportions of acid in the product can be removed by treatment with alkali before distillation.

Using the process of this invention, maleic anhydride or succinic anhydride is converted virtually quantitatively in a simple reaction. The yields of tetrahydrofuran achieved are greater than 90 mole percent, e.g. 91–98 mole percent. The formation of non-utilizable by-products is slight. Tetrahydrofuran which is more than 99.5 percent pure can be recovered and separated from the reaction products by fractional distillation. Additionally, by adjusting the process parameters of temperature and/or pressure 1,4-butanediol and gamma-butyrolactone in addition to tetrahydrofuran can be produced in recoverable quantities.

Although the preceding description is given in terms of a continuous process, if desired, the process of this invention may be carried out in batch mode employing conditions corresponding to those specified above. Without further elaboration, it is believed that one skilled in the art can, using the preceding description, can utilize the present invention to its fullest extent.

SPECIFIC EMBODIMENT

The following preferred embodiments are to be construed as merely illustrative, and not limitative of the remainder of the disclosure in any way whatsoever.

EXAMPLES 1–4

Cu/ZnO/Al$_2$O$_3$/Cr$_2$O$_3$ Hydrogenation Catalyst

A catalyst comprising the mixed oxides of copper, zinc, aluminum and chromium is employed in Examples 1–4. The oxidized form of this catalyst is of the general formula CuO/ZnO/Al$_2$O$_3$/Cr$_2$O$_3$ and is commercially available from United Catalysts, Inc. (No. T-2107). The nominal compositions of the unreduced catalyst is as follows:

Copper Oxide 40–50 wt%
Zinc Oxide 10–20 wt%
Alumina 20–30 wt%
Chrome Oxide 1–5 wt%

This catalyst has an empirical formula of $Cu_{1.0}Al_{1.2}Zn_{0.4}Cr_{0.04}O_x$.

Additionally, Example 4 employs a cocatalyst comprising the mixed oxides of copper and chromium. The oxidized form of this catalyst is of the general formula CuO/Cr$_2$O$_3$/BaO and is commercially available from Harshaw/Filtrol Inc. (No. 1107T). The nominal composition of the unreduced and untreated catalyst is as follows:

Copper Oxide 33 wt%
Chrome Oxide 38 wt%
Barium Oxide 9 wt%

This catalyst has an empirical formula of $Cu_{1.0}Cr_{1.2}Ba_{0.14}O_x$.

Both catalysts were received in ⅛" pellet form. The pellets were ground and sieved to obtain 10/30 mesh fractions which were used for catalyst testing.

The CuO/Cr$_2$O$_3$/BaO catalyst was extracted for 48 hours with hot water in a Soxhlet extractor to remove water soluble chromium species. The catalyst was then dried overnight in an oven at 120° C.

Prior to testing, the catalysts were reduced at 250° C. and atmospheric pressure, with a gas mixture of 5% H$_2$ in N$_2$ flowing over the catalyst at a rate of 1 SLM.

The liquid feeds were prepared by dissolving maleic or succinic anhydride in ethanol or butanol. The mixtures were heated to aid dissolution of the anhydrides.

The catalysts were tested in a fixed-bed reactor system with the liquid feed and hydrogen being co-currently at the top of the reactor. The process parameters and feed conditions for each example are summarized below:

EXAMPLE 1

Hydrogenation of 20%(W/V) Maleic Anhydride Over Cu/ZnO/Al$_2$O$_3$/CrO$_3$ Catalyst With CO in H$_2$ 20 cc of the CuO/ZnO/Al$_2$O$_3$/Cr$_2$O$_3$ catalyst (21.4 g) was loaded into the reactor. After reduction, the system was pressurized to 600 psig with a gas feed of 8% CO in H$_2$. The details and results of the catalyst testing at 235 and 218° are summarized in Table 1 below:

TABLE 1

Hydrogenation of 20% MAH/EtOH over Cu/ZnO/Al$_2$O$_3$/Cr$_2$O$_3$ with 8% CO in Feed

| Temperature, °C. | 235 | 218 |
|---|---|---|
| Catalyst Age, h | 24 | 72 |
| Selectivities | | |
| Butanediol | 0 | 30.1 |
| THF | 94.1 | 43.2 |
| Butyrolactone | — | 24.3 |
| Butanol | 4.2 | 1.5 |
| Propanol | 1.1 | 0.4 |
| Diethylsuccinate | — | 0.2 |
| CO$_2$ + CH$_4$ | 0.7 | 0.4 |

P = 600 psig; LHSV = 0.32 h$^{-1}$; GHSV = 4000 h$^{-1}$
The liquid product contained 23% methanol at 235° C., and 1.4% methanol at 218° C.

EXAMPLE 2

Hydrogenation of 40%(W/V) Maleic Anhydride/Ethanol Over Cu/ZnO/Al$_2$O$_3$/Cr$_2$O$_3$ Catalyst With CO in H$_2$ Feed 25 cc of the CuO/ZnO/Al$_2$O$_3$/Cr$_2$O$_3$ catalyst (28.4 g) was loaded into the reactor and reduced. The system was then pressurized to 600 psig with a feed of 12% CO in H$_2$. The results of catalyst testing at 250° C. are shown in Table 2 below:

TABLE 2

Hydrogenation of Maleic Anhydride in Ethanol (40% W/V) Over Cu/ZnO/Al$_2$O$_3$/Cr$_2$O$_3$ with 12% CO in Feed Gas

| Catalyst Age, h | 24 |
|---|---|
| Selectivities | |
| Butanediol | 0 |
| THF | 94.3 |
| Propanol | 1.2 |
| Butanol | 4.2 |
| CO$_2$ + CH$_4$ | 0.3 |

600 psig; GHSV = 2900 h$^{-1}$, LHSV = 0.26 h$^{-1}$
The liquid product also contained ~48% methanol from the hydrogenation of carbon monoxide in the feed gas.

EXAMPLE 3

Hydrogenation of 20%(W/V) Succinic Anhydride/Ethanol Over Cu/ZnO/Al$_2$O$_3$/Cr$_2$O$_3$ Catalyst (No CO in feed)

20 cc of the CuO/ZnO/Al$_2$O$_3$/Cr$_2$O$_3$ catalyst (22.2 g) was loaded into the reactor and reduced. The results of catalyst testing at 235° C. are given in Table 3 below:

TABLE 3

Hydrogenation of Succinic Anhydride in Ethanol 20% (W/V) Over Cu/ZnO/Al$_2$O$_3$/Cr$_2$O$_3$ at 235° C.

| Liquid Feed | 20% SAH in EtOH | |
| --- | --- | --- |
| Catalyst Age, h | 48 | 189 |
| Selectivities | | |
| Butanediol | 0.3 | 0.4 |
| THF | 94.4 | 94.8 |
| Propanol | 0.2 | 0.1 |
| Butanol | 3.7 | 3.8 |
| Butyrolactone | 1.1 | 0.6 |
| CO$_2$ + CH$_4$ | 0.3 | 0.3 |

P = 600 psig; GHSV = 4000 h$^{-1}$; LHSV = 0.34 h$^{-1}$

EXAMPLE 4

Hydrogenation of 19.6%(W/V) Succinic Anhydride/Butanol Over CuO/ZnO/Al$_2$O$_3$/Cr$_2$O$_3$ and CuO/Cr$_2$O$_3$/BaO (No CO)

10 cc (14.1 g) of Cu/Cr$_2$O$_3$/BaO and 15 cc (16.4 g) of CuO/ZnO/Al$_2$O$_3$/Cr$_2$O$_3$ were placed in the reactor with the CuO/Cr$_2$O$_3$/BaO placed above the CuO/Cr$_2$O$_3$/Al$_2$O$_3$/BaO. The system was tested over a 220 h period at 235° C. with LHSV's ranging from 0.27 to 0.48 h$^{-1}$. The results are shown in Table 4 below. The combination catalyst system gave improved catalyst stability.

TABLE 4

Hydrogenation of a 19.6% (W/V) SAH/Butanol Feed Over Copper Chromite + Cu/ZnO/Al$_2$O$_3$/Cr$_2$O$_3$ Combination Catalyst

| Reaction Temperature, °C. | 235 | 235 | 235 | 235 | 220 |
| --- | --- | --- | --- | --- | --- |
| LHSV, h$^{-1}$ | 0.27 | 0.34 | 0.41 | 0.48 | 0.27 |
| GHSV, h$^{-1}$ | 3200 | 3200 | 3200 | 3200 | 3200 |
| Catalyst Age, h | 19 | 223 | 247 | 271 | 408 |
| Selectivity, % | | | | | |
| THF | 99.1 | 97.0 | 92.3 | 81.1 | 49.7 |
| Butanediol | 0 | 2.0 | 2.9 | 7.3 | 26.4 |
| Butyrolactone | 0 | 0.6 | 4.7 | 11.5 | 23.8 |
| Propanol | 0.2 | 0.2 | 0.1 | 0.1 | 0.1 |
| CO$_2$ + CH$_4$ | 0.7 | 0.2 | — | — | — |

P = 600 psig
Liquid product also contained 0.2–0.6% Butylbutyrate. Selectivities do not include Butanol from Succinic Anhydride since butanol is the solvent.

The claimed invention is:

1. A continuous single stage process for the preparation of tetrahydrofuran comprising catalytically hydrogenating the solution which results when at least one of maleic anhydride or succinic anhydride is dissolved in a lower monohydric alcohol, wherein the hydrogenation is carried out in the presence of a hydrogen containing gas and a hydrogenation catalyst of the formula $$Cu_1Zn_bAl_cM_dO_x$$

wherein M is at least one element selected from the group consisting of Groups IIA thru IIIA, Group VA, Group VIII, Ag, Au, Groups IIIB thru VIIB, the Lanthanum Series, and the Actinium Series;
0.001 < b < 500;
0.001 < c < 500;
0 < d < 200; and
x is the number of oxygen atoms necessary to satisfy the valency requirement of the other elements.

2. The process of claim 1, wherein the hydrogenation catalyst is a two-component catalyst system comprising (i) the mixed oxides of copper, zinc and aluminum and (ii) the mixed oxides of copper and chromium.

3. The process of claim 1, wherein the alcohol is a monohydric aliphatic alcohol.

4. The process of claim 3, wherein the alcohol is a C$_1$ to C$_{20}$ aliphatic alcohol.

5. The process of claim 4, wherein the alcohol is n-butanol or isobutanol.

6. The process of claim 1, wherein the molar ratio of the anhydride to alcohol is between 1:2 and 1:15.

7. The process of claim 1, wherein the solution is between 10 and 80 weight percent of at least one of maleic anhydride or succinic anhydride in the alcohol.

8. The process of claim 1, wherein the hydrogen to the anhydride feed ratio is between about 100 to 1 and 500:1.

9. The process of claim 1, wherein the hydrogenation is carried out at a pressure in the range of 10 to 100 atmospheres and at a temperature in the range of 200° C. to 325° C.

10. A continuous single stage process for the preparation of tetrahydrofuran in yields greater than 90 mole percent, comprising catalytically hydrogenating the solution which results when at least one of maleic anhydride or succinic anhydride is dissolved in a lower monohydric alcohol, wherein the hydrogenation is carried out in the presence of a hydrogen containing gas and a hydrogenation catalyst containing the mixed oxides of copper, zinc and aluminum, wherein said catalyst consists essentially of 40 to 50 wt% copper oxide, 10–20 wt% zinc oxide, 20–30 wt% aluminum oxide and 1–5 wt% of chromium oxide.

* * * * *